United States Patent
Tzidon et al.

(10) Patent No.: US 8,248,255 B2
(45) Date of Patent: Aug. 21, 2012

(54) OPTICAL FLUID TESTER

(75) Inventors: Aviv Tzidon, Tel Aviv (IL); Yehuda Yavets-Chen, Caesaria (IL); Dekel Tzidon, Hod Hasharon (IL)

(73) Assignee: Verifuel Ltd., Rosh Ha'ain (IL)

( * ) Notice: Subject to any disclaimer, the term of this patent is extended or adjusted under 35 U.S.C. 154(b) by 368 days.

(21) Appl. No.: 12/577,768

(22) Filed: Oct. 13, 2009

(65) Prior Publication Data

US 2011/0084842 A1 Apr. 14, 2011

(51) Int. Cl.
*G08B 21/00* (2006.01)
(52) U.S. Cl. .......................................... 340/603; 356/436
(58) Field of Classification Search .................. 340/603; 356/436

See application file for complete search history.

(56) References Cited

U.S. PATENT DOCUMENTS

| | | | |
|---|---|---|---|
| 7,408,632 B2* | 8/2008 | Moore | 356/134 |
| 7,880,133 B2* | 2/2011 | Johansen | 250/266 |
| 8,040,498 B2* | 10/2011 | Gan | 356/128 |
| 2002/0135765 A1 | 9/2002 | Darrow et al. | |
| 2003/0127609 A1* | 7/2003 | El-Hage et al. | 250/574 |
| 2005/0136548 A1 | 6/2005 | McDevitt et al. | |
| 2008/0309937 A1* | 12/2008 | Gan | 356/364 |
| 2009/0128803 A1 | 5/2009 | Gan | |
| 2009/0153846 A1* | 6/2009 | Gan et al. | 356/133 |

FOREIGN PATENT DOCUMENTS

WO WO 2005/050179 6/2005

OTHER PUBLICATIONS

International Search Report for PCT Application No. PCT/IL2010/000836 mailed on Feb. 10, 2011.

* cited by examiner

*Primary Examiner* — Eric M Blount
(74) *Attorney, Agent, or Firm* — Pearl Cohen Zedek Latzer LLP

(57) ABSTRACT

An optical fluid tester device for testing a fluid sample in an ampoule includes an ampoule cradle, a radiation source, a radiation detector and an analyzer. The ampoule cradle supports the ampoule. The ampoule with the fluid sample serves as a lens whose focal properties are dependent on the index of refraction of the fluid sample. The radiation source irradiates the ampoule. The radiation detector is located opposite the radiation source so that the ampoule, when supported by the ampoule cradle, lies between the radiation source and the radiation detector. The detector serves to detect the intensity of the incident radiation. The analyzer verifies the composition of the fluid sample based on the detected intensity, which is dependent on the focal properties of the ampoule and is, therefore, indicative of the composition of the fluid sample.

17 Claims, 7 Drawing Sheets

OPTICAL FLUID TESTER

FIELD OF THE INVENTION

The present invention relates to fluid testing. More particularly, the present invention relates to an optical fluid tester.

BACKGROUND OF THE INVENTION

Fluid testing covers a large variety of tests aimed at detecting the presence of specific fluids or identifying certain fluids. Fluid testing may include, for example, water purity tests, industrial quality tests, and aviation fuel purity tests.

Checking the quality of aviation fuel is a routine practice. Poor fuel quality may lead to loss of engine power, possibly resulting in an aviation accident. Aviation regulations stipulate that fuel should be checked daily by ground personnel, and as part of the preflight checks performed by a pilot. With some aircraft (such as, for example small airplanes), these checks are performed by taking samples directly from the fuel system. For example, a fuel sample is typically collected from the bottom of the fuel tank into an ampoule. The sample in the ampoule is then checked visually. A typical procedure for checking for water in the fuel is based on a visual detection of the difference in color between water and fuel. Such a visual determination may be dependent on a subjective interpretation of the visual results. Interpretation of the results may be affected by such factors as, for example, illumination of the sample, the experience of the pilot or other person performing the check, and the condition of the ampoule.

Fuel may also be visually checked for other properties. For example, since aviation fuel is typically dyed to indicate the type and grade of the fuel, the color of the fuel may be compared against known fuel colors.

Checking the quality of the fuel may be assisted by an appropriate optical device. For example, the index of refraction of fuel may be different than the index of refraction of water. In addition, the indices of refraction of various types or grades of fuel may differ from one another. Thus, an appropriate device that is sensitive to index of refraction may be used to assist in checking fuel quality. In order to reduce subjectivity in interpreting the results, it may be advantageous if the device were automated. An automated device may give an automatically generated indication as to whether or not the fuel quality is acceptable.

Gan, in WO 2005/050179 and in US 2009/0128803, has described optical devices that may be used to check for deviation of the index of refraction of a fluid from an expected value. In the described optical devices, the fluid to be checked is introduced into the optical path of a device in which two or more gratings or similar patterns are observed. Light passing through the gratings and the fluid form a moiré pattern. The details of the moiré pattern formed by the device are sensitive to the index of refraction of the fluid. Therefore, visual or automated comparison of the observed moiré pattern with a reference moiré pattern may indicate whether the index of refraction has an expected value. However, automated comparison of moiré patterns may require a complex comparison device and algorithm. In addition, an automated moiré pattern comparison may be sensitive to variable factors other than index of refraction.

Gan et al. in US 2009/0153846 describe an optical dipstick device that may be lowered into a fluid. In the optical dipstick device, the end of the dipstick is inserted into a container for containing a fluid. The optical path from a light source to a detector or to a detector array in the dipstick depends on the optical properties of the contents of the container. Thus, a detector signal may be interpreted to indicate the quantity of fluid present in the container, and whether the index of refraction of a fluid in the container matches an expected value. However, such a dipstick device may be inconvenient for use with a typical fuel ampoule.

It is an object of the present invention to provide a device for automatic optical checking of fuel quality.

Other aims and advantages of the present invention will become apparent after reading the present invention and reviewing the accompanying drawings.

SUMMARY OF THE INVENTION

There is thus provided, in accordance with some embodiments of the present invention, an optical fluid tester device for testing a fluid sample in an ampoule. The device includes an ampoule cradle for supporting the ampoule, the ampoule with the fluid sample serving as a lens whose focal properties are dependent on the index of refraction of the fluid sample. The device further includes a radiation source for irradiating the ampoule, and a radiation detector located opposite the radiation source, so that the ampoule, when supported by the ampoule cradle, lies between the radiation source and the radiation detector, the detector serving for detecting intensity of incident radiation. The device further includes an analyzer for verifying the composition of the fluid sample based on the detected intensity which is dependent on the focal properties of the ampoule, thereby indicative of the composition of the fluid sample.

Furthermore, in accordance with some embodiments of the present invention, the device includes an illuminator lamp for illuminating the fluid sample in the ampoule.

Furthermore, in accordance with some embodiments of the present invention, the illuminator lamp is configured so as to illuminate the fluid sample from below the ampoule and an area above an opening of the ampoule.

Furthermore, in accordance with some embodiments of the present invention, the ampoule cradle allows visual inspection of the ampoule and the fluid inside.

Furthermore, in accordance with some embodiments of the present invention, the radiation source is configured to emit radiation with a spectral range of 800 nm to 1000 nm.

Furthermore, in accordance with some embodiments of the present invention, the analyzer is configured to distinguish between water and a fuel.

Furthermore, in accordance with some embodiments of the present invention, the device includes an indicator for indicating the composition of the fluid sample.

Furthermore, in accordance with some embodiments of the present invention, the indicator includes a blinking white lamp for indicating an acceptable composition.

Furthermore, in accordance with some embodiments of the present invention, the alarm includes a flashing red lamp for indicating an unacceptable composition.

Furthermore, in accordance with some embodiments of the present invention, the device includes a circuitry for verifying an operational condition of the device.

Furthermore, in accordance with some embodiments of the present invention, the device includes a light emitting diode assembly for indicating the operation condition.

Furthermore, in accordance with some embodiments of the present invention, the radiation source is configured to emit radiation with a predetermined pulse pattern and wherein the analyzer is configured to verify the composition of the fluid sample based on detected intensity with a pulse pattern substantially matching the predetermined pulse pattern.

Furthermore, in accordance with some embodiments of the present invention, the radiation source is configured to emit a diverging beam of radiation.

Furthermore, in accordance with some embodiments of the present invention, the device is configured to be operated by pressing on a single pushbutton.

Furthermore, in accordance with some embodiments of the present invention, the device is configured to distinguish between a short press and a long press on the pushbutton, such that operation of the device is controllable by the length of the press.

Furthermore, in accordance with some embodiments of the present invention, the device is configured to run a self test when the verified composition is consistent with the composition of the contents of an empty ampoule.

Furthermore, in accordance with some embodiments of the present invention, the radiation detector includes at least two sensors positioned at different heights.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF EMBODIMENTS

Figure 1A:
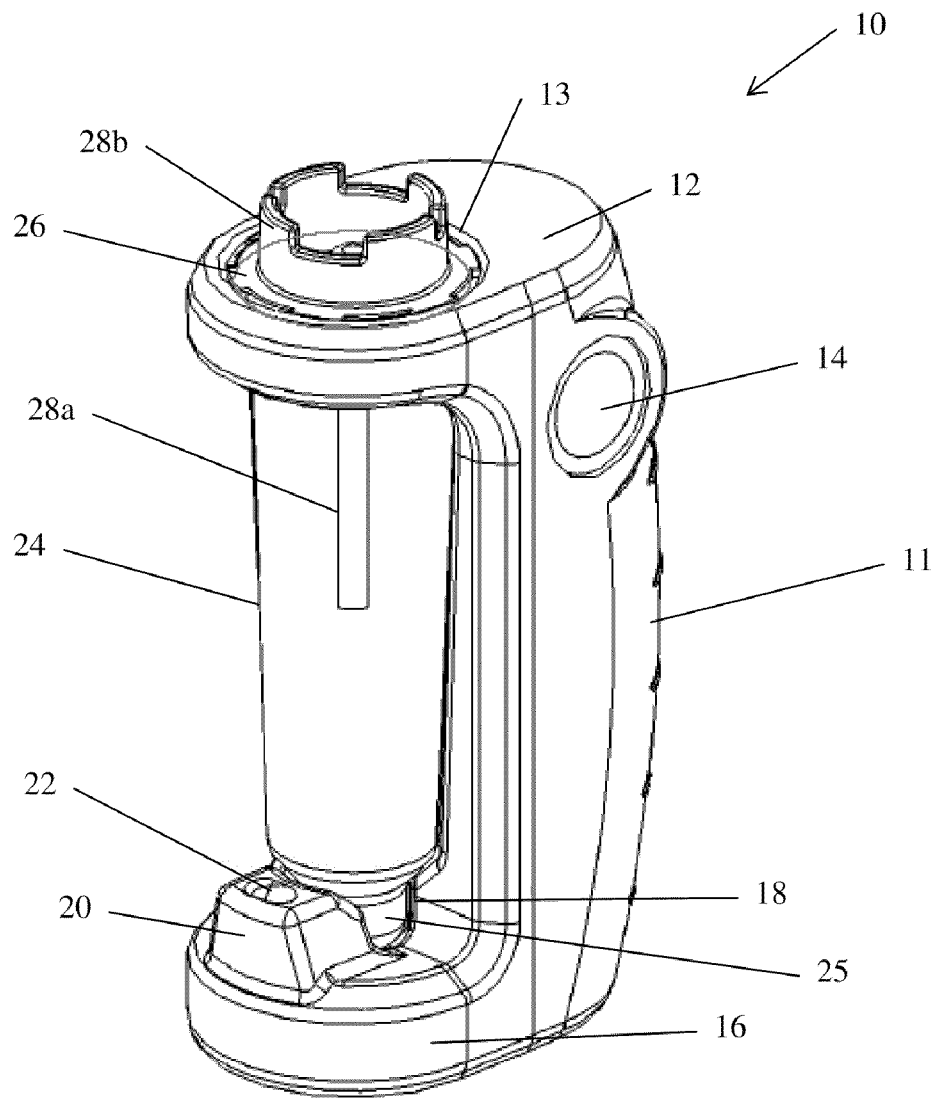
FIG. 1A shows a fluid tester with an inserted ampoule, in accordance with embodiments of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

A fluid tester in accordance with embodiments of the present invention is designed to test the quality of a fluid, such as fuel drained from a fuel tank of an aircraft, based on the index of refraction of the fluid. The fluid tester includes a holder, such as a cradle, for holding an ampoule. The walls of the ampoule are substantially transparent to radiation of at least one spectral range. The ampoule may be filled with air or with a fluid sample to be tested. The ampoule may be provided with one or more accessories for facilitating drainage of contents of a fuel tank into the ampoule. For example, the accessories may include a tube for opening a drain valve of a fuel tank and conducting a fluid sample from the drain valve into the ampoule. For example, a cover or cap for the ampoule may be provided with an extension for draining a fluid sample from a particular type of drain valve. Typically, the cover may be reversible and may be provided with two extensions, one on either side of the cover. Each extension may be adapted to draining a fluid sample from a different type of valve. The extension that is in use extends outward from the cover, while the other extension extends into the interior of the ampoule. Thus, the extension not in use is stored in a convenient manner.

A fluid tester in accordance with embodiments of the present invention may be provided with one or more illumination sources. For example, an illumination source, such as a lamp, may be provided to illuminate the ampoule so as to facilitate visual inspection of the fluid sample in the ampoule. Such an illumination source may be typically located below a transparent bottom surface of the ampoule when ampoule is held in ampoule holder. Thus, the illumination source may effectively illuminate the length of the ampoule. Such lengthwise illumination may enhance any boundaries between layers of different types of fluids within the ampoule. In addition, the illumination source may be operated to illuminate a fuel tank drain valve. Illuminating a drain valve may facilitate draining fuel into the ampoule, especially at night or when the drain valve is located in a shaded location.

A fluid tester in accordance with embodiments of the present invention may be provided with an automatic testing device for checking the index of refraction of the ampoule with its contents. An automatic testing device may include a radiation source and a detector assembly. An ampoule to be tested is held by an ampoule cradle between the radiation source and the detector assembly. The detector assembly is designed to detect radiation of the spectral range emitted by the radiation source. The spectral range of the radiation is selected such that a typical fluid to be tested, such as an aircraft fuel, as well as any potential contaminating or substituted fluids, such as, for example, water or a different grade of aircraft fuel, are substantially transparent to the radiation. In addition, the spectral range may be selected such that the difference in index of refraction between an acceptable composition of a fluid sample and an unacceptable composition is detectable by the apparatus.

The ampoule with its contents typically acts as a lens with particular focal properties. An ampoule typically is shaped as an elongated cylinder with an annular cross section, such that the ampoule acts as a converging lens. Thus, a non-meridional skew ray of radiation that traverses the ampoule is bent toward the longitudinal axis of the ampoule. Thus, radiation that traverses the ampoule tends to converge. The focal properties of the ampoule, such as the degree of convergence, may depend on the index of refraction of the fluid sample in the ampoule. As the index of refraction of the fluid sample increases, the bending of a skew ray that traverses the fluid also increases. Typically, an automatic testing device may be configured for operation with a particular design (for example, particular shape, dimensions, and material) of ampoule. Alternatively, the automatic testing device may be configured for operation with a predetermined assortment of ampoule designs.

For example, a radiation source of the automatic testing device may emit a diverging beam of radiation toward a side of the ampoule. One or more radiation detectors of a detector assembly may be located on the side of the ampoule opposite the radiation source. Each radiation detector produces a signal that indicates the intensity of radiation that impinges on the surface of that detector. The ampoule may cause the radiation emitted by the radiation source to converge toward the detector assembly. Typically, the intensity of the radiation impinging on each detector surface may depend, among other factors, on the amount of convergence by the ampoule. The amount of convergence is generally influenced by the index of refraction of the fluid sample in the ampoule. Therefore, the signal produced by the radiation detector may be associated with a particular composition of the fluid sample. Thus, the automatic testing device may be calibrated to distinguish among several fluid compositions. For example, the automatic testing device may be calibrated to distinguish between fuel and water.

Alternatively, other optical configurations are possible. For example, the radiation source may emit a parallel or converging beam, while surface of the section of the ampoule that is traversed by the beam may be concave, acting as a diverging lens. In such cases, the intensity of radiation incident on the detector may be associated in a different manner with the optical properties of the fluid sample. As another example, the detector assembly may include a one or two dimensional array of detectors. In such a case, the composition of a fluid sample may be associated with a particular distribution of intensity as detected by the detector array.

The radiation incident on the detector may include ambient radiation from the environment, for example solar radiation, or other stray radiation. Only the radiation that is emitted by the source and reaches the detector may correlate with the index of refraction of the ampoule contents. Therefore, it may be necessary to separate a detector signal due to radiation from the source from other sources of detector signal, such as ambient or stray light. One option is to provide covers or shielding to prevent stray radiation from reaching the radiation detector. Another solution may enable distinguishing between radiation emitted by the radiation source and stray radiation. Typically, an automatic testing device may be configured such that radiation from the radiation source reaches the radiation detector intermittently at predetermined intervals. For example, radiation emitted by the radiation source may be pulsed or chopped. An appropriate processor or circuit, as known in the art, may then be used to extract the signal due to the radiation emitted by the radiation source from a total detector signal.

The detector signal may be further processed or analyzed. For example, the signal may be analyzed to determine whether or not the composition of the fluid sample in the ampoule is acceptable. Analysis processing, for example, may distinguish between a detector signal that correlates with a desired composition of the fluid sample, for example a particular grade of fuel, or an undesirable composition, for example water or a different grade of fuel.

Analysis processing may be performed by an appropriate analyzer associated with a controller. An appropriate controller may include a processing device, such as an appropriate programmed processor or circuitry, and circuitry for operate one or more indicator devices. The indicator devices may be operated to indicate whether or not the composition of the fluid sample in the ampoule is acceptable. Such indicator devices may include devices that generate a visible, audible, palpably sensible, or other form of signal. A visible signal may include, for example, a displayed text, a dial indicator, a steady or flashing light of a particular color, or other visible indication known in the art. An audible signal may include a vibrator, buzzer, tone, bell, alarm, click, simulated or recorded speech, or other audible signal. A palpably sensible signal may include a vibration, pulsing, or shaking. For example, in a typical configuration, an acceptable composition may be indicated by a slowly blinking white light that illuminates the ampoule. An unacceptable composition may be indicated by a rapidly flashing red light, and a vibrator that generates both an audible and a palpably sensible signal.

A fluid tester in accordance with embodiments of the present invention may include test circuitry for performing one or more self tests for determining the operational status of the fluid tester. For example, the circuitry may include circuitry for testing the status of a power source, such as batteries, and correct operation of electro-optical components. For example, self testing may be initiated when powering on the fluid tester or when the automatic testing device determines that the ampoule is empty.

Reference is now made to the accompanying Figures.

Figure 1B:
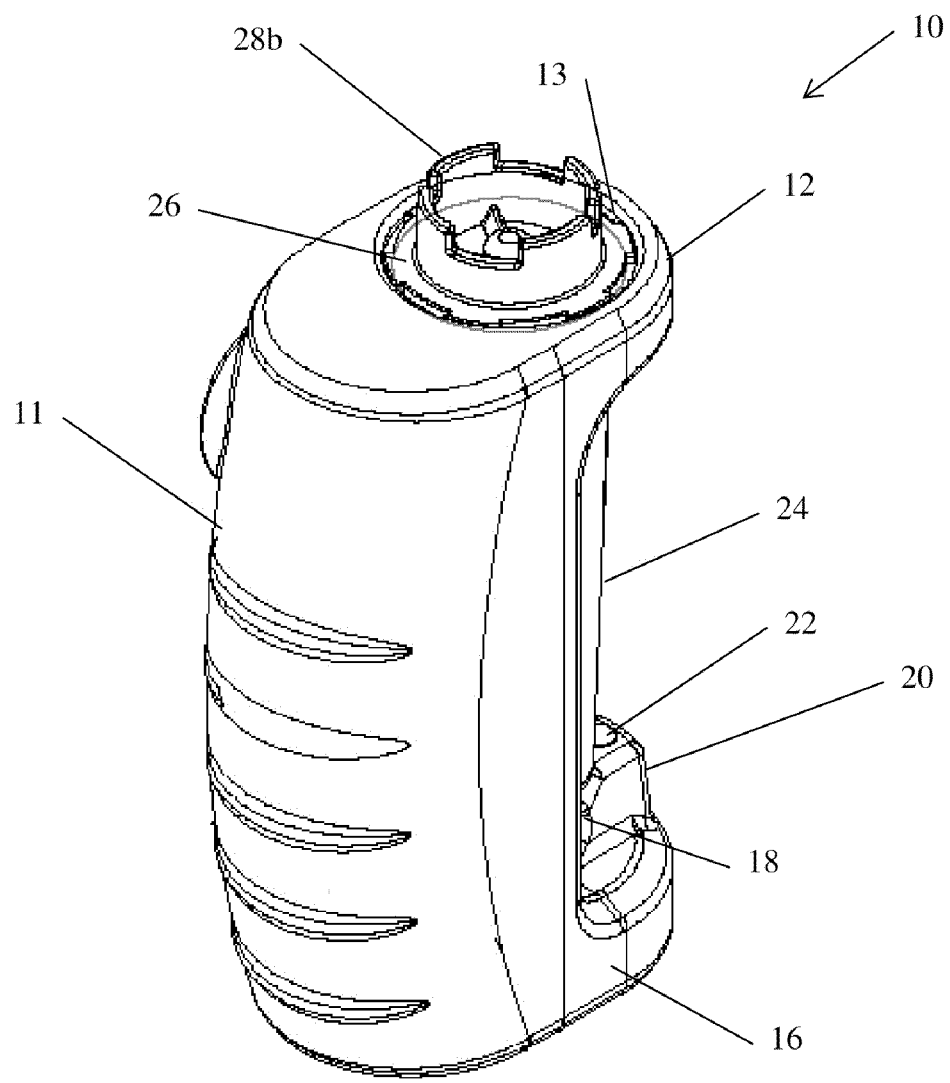
FIG. 1B shows another view of the fluid tester shown in FIG. 1A.
Figure 1C:
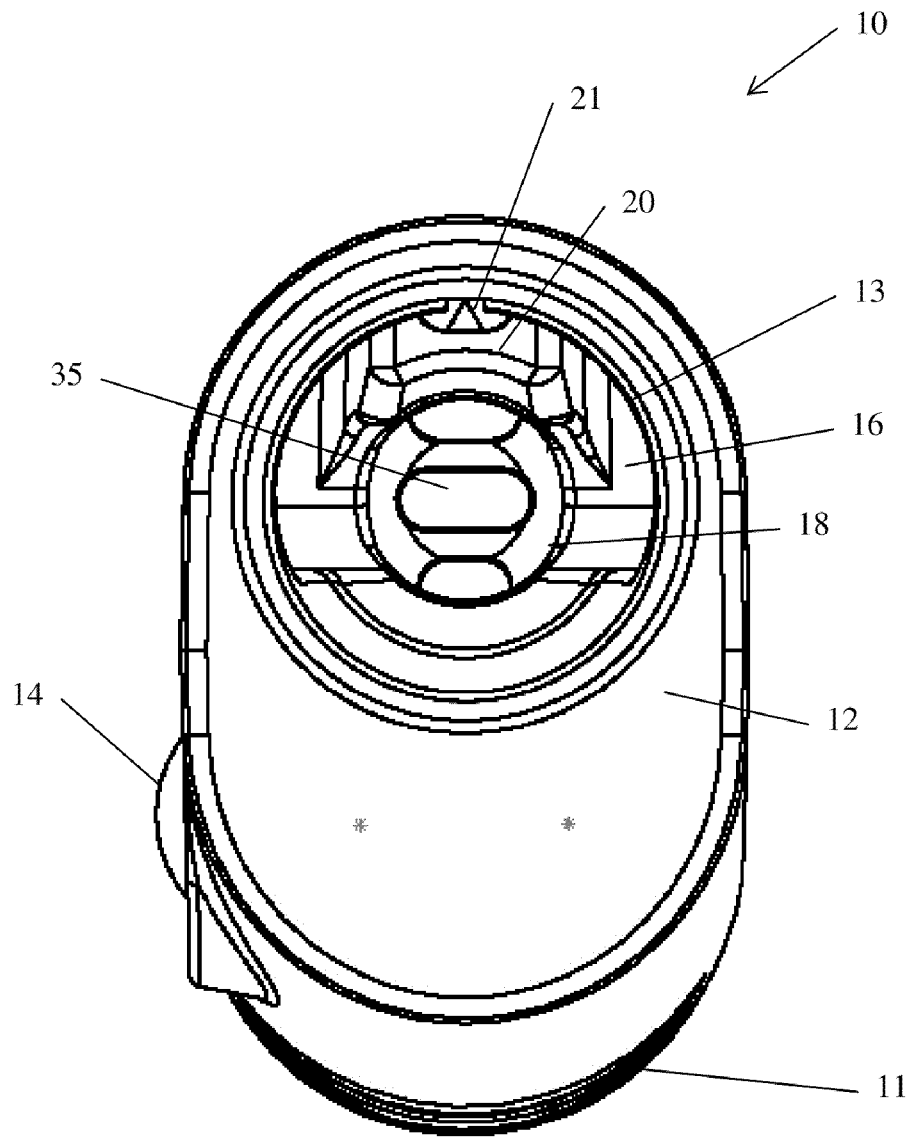
FIG. 1C shows a top view of the fluid tester shown in FIG. 1A with the ampoule removed.
Figure 1D:
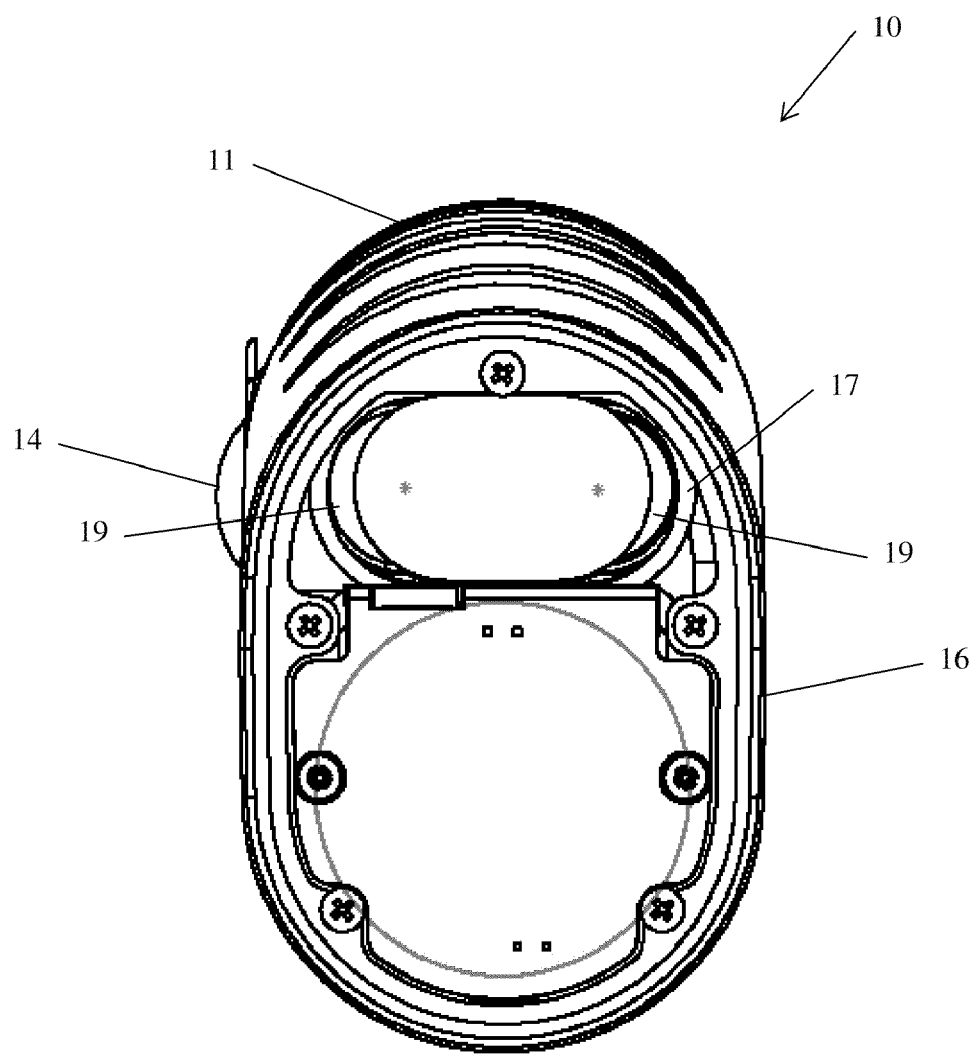
FIG. 1D shows a bottom view of the fluid tester shown in FIG. 1A.

FIG. 1A shows a fluid tester with an inserted ampoule, in accordance with embodiments of the present invention. FIG. 1B shows another view of the fluid tester shown in FIG. 1A. FIG. 1C shows a top view of the fluid tester shown in FIG. 1A with the ampoule removed. FIG. 1D shows a bottom view of the fluid tester shown in FIG. 1A. Fluid tester 10 is enclosed by housing 11. Housing 11 includes tester base 16 and top section 12. A removable ampoule 24 may held in place in fluid tester 10 by opening 13 in top section 12, and by ampoule cradle 18 in tester base 16. Opening 13 may be provided with notch 21. Ampoule 24 may be provided with a tab (not shown) that is designed to fit into notch 21. Thus, the tab on ampoule 24, together with notch 21, may ensure a reproducible orientation of ampoule 24 when held by fluid tester 10.

Ampoule cover 26 fits into opening 13 of top section 12. Narrow extension 25 of ampoule 24 fits into ampoule cradle 18 in tester base 16. Ampoule cover 26 includes narrow extension 28a and crenellated extension 28b. Narrow extension 28a and crenellated extension 28b are each adapted to open variously configured valves that are commonly found on aircraft fuel systems. Pressing either narrow extension 28a or crenellated extension 28b against a corresponding structure on an appropriately configured valve may enable operation of the valve. Operation of the valve may enable draining a fluid sample from a fuel system, fuel tank, or other fluid container into ampoule 24. Ampoule cover 26 may be inverted on ampoule 24 such that either narrow extension 28a or crenellated extension 28b extends outward.

Fluid tester 10 may include one or more electrically powered devices. Electrically powered devices may include illumination devices, indicator lights or devices, and automatic testing devices. Power for electrically powered devices may be typically provided by batteries 19 in battery compartment 17 of tester base 16 (FIG. 1D). Alternatively, electrical power may me provided by connecting to an electrical power grid, possibly through an appropriate adapter circuit.

An indicator device, such as indicator light emitting diode (LED) assembly 22, may include one or more LED devices adapted to emit light of different colors. For example, indicator LED assembly 22 may be operated to indicate the status of batteries 19. For example, a circuit of fluid tester 10 may be configured to measure the voltage output of batteries 19 using circuitry and methods known in the art. For example, in a typical configuration, indicator LED assembly 22 may glow green when the voltage of batteries 19 is above a predetermined level. For example, for a typical fluid tester 10, indicator LED assembly 22 may glow green when battery voltage exceeds 2.5 V, indicating a sufficiently fully charged battery. A weak battery, with voltage in the range of 2.2 V to 2.5 V may be indicated by indicator LED assembly 22 glowing red. A battery that is too weak for proper operation of fluid tester 10, for example, with voltage less than 2.2 V, may generate an alarm indication by causing indicator LED assembly 22 to flash red. When the battery is too weak for proper operation, a controller of fluid tester 10 may follow the alarm indication by automatic extinguishing of fluid tester 10. Other colors emitted by indicator LED assembly 22 may indicate other situations requiring attention. For example, in a typical configuration, indicator LED assembly 22 may glow orange to indicate an electro-optic failure of the automatic testing optics, such as, excess opacity of the ampoule or optics due to, for example, darkening, soiling, or smudging, or another optic failure.

Fluid tester 10 may be operated by operating appropriate controls. For example, a typical configuration may include a single control in the form of pushbutton 14 that performs several functions. Such functions may include, for example, illuminating an ampoule for visual inspection, performing a system self test, and initiating an automatic test of the contents of an ampoule. Alternatively, a separate control may be provided for each function of fluid tester 10.

For example, in a typical configuration, a short push on pushbutton 14 may cause an illumination device to turn on or off. For example, in a typical configuration, illuminator 35, (FIG. 1C) located at the bottom of ampoule cradle 18, may house one or more illumination sources. Typically, at least one of the illumination sources is and illumination source capable of emitting white light. The illumination source may be toggled on or off by successive short pushes of pushbutton 14.

In a typical configuration of fluid tester 10, pressing pushbutton 14 for longer than a predetermined period of time, for example 1.5 seconds, operates an automatic testing assembly. The automatic testing assembly may typically be located in tester base 16 and structure 20. Operation of the automatic testing assembly typically entails operating a radiation source, a detector assembly, and detector signal analysis processing. In a typical configuration, the automatic testing assembly may run a self test of systems of fluid tester 10 when a detector signals indicates that an inserted ampoule is empty.

Figure 2:
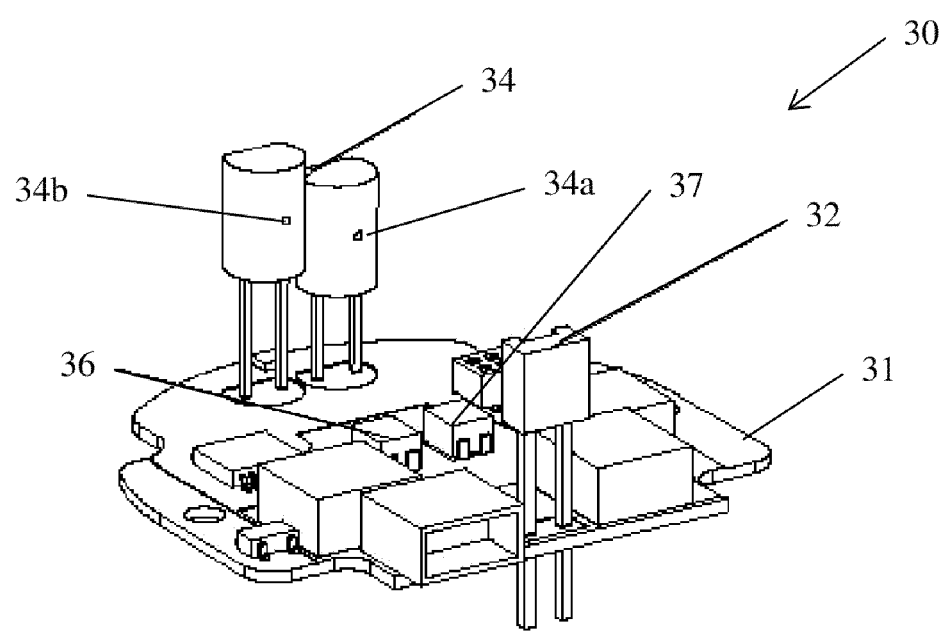
FIG. 2 shows a tester assembly in accordance with embodiments of the present invention.

FIG. 2 shows a tester assembly in accordance with embodiments of the present invention. Tester assembly 30 includes various electronic components, including illumination source components of illuminator 35 (FIG. 1C), and components of an automatic testing device. Components of tester assembly 30 are mounted on circuit board 31.

Illumination source components of illuminator 35 may typically include one or more white light sources, such as white lamp 36, and one or more a colored light sources, such as red lamp 37. For example, white lamp 36 may be turned on to illuminate an ampoule for visual examination of the ampoule's contents. An ampoule may be provided with one or more magnifying elements for facilitating visual examination of the ampoule's contents. In addition, white lamp 36 may be operated or blinked as an indicator, such as to indicate an acceptable fluid composition. Red lamp 37 may be operated to illuminate an ampoule as an indicator. For example, red lamp 37 may be flashed to indicate an unacceptable fluid composition.

An automatic testing device includes one or more radiation sources, such as radiation source 32, and a detector assembly 34. Radiation source 32 may emit diverging radiation in the form of an approximately conical funnel-shaped, or a flattened fan-shaped, beam. The conical shape may be defined by its apex angle, defining the angular spread of the beam. For example, in a typical configuration, the angular spread of the beam may be defined by a half-angle of about 25°, or a full angular spread of about 50°. Typically, the angular spread may be sufficient such as to irradiate the entire perimeter of narrow ampoule extension 25 of ampoule 24 (FIG. 1A), when ampoule extension 25 is located in ampoule cradle 18. Radiation source 32 may be designed to emit radiation in a particular spectral band. For example, in a typical fluid tester, radiation source 32 may emit radiation in a near infrared spectral band from about 800 nanometers (nm) to about 1000 nm, with a spectral peak at about 940 nm.

Detector assembly 34 may include two or more detectors, such as detectors 34a and 34b. In a typical configuration, one detector, such as detector 34b, is positioned above (further from circuit board 31 than) another detector 34a. For example, in a typical configuration, detector 34b may be positioned approximately 2 mm above detector 34a. For example, such a placement may be beneficial if a boundary between layers of water and of fuel, or an obstruction, blocks an optical path between radiation source 32 and one of either detector 34a or 34b. In such an event, tiered placement of detectors 34a and 34b may ensure that a valid signal is generated by at least one of detectors 34a or 34b.

Figure 3:
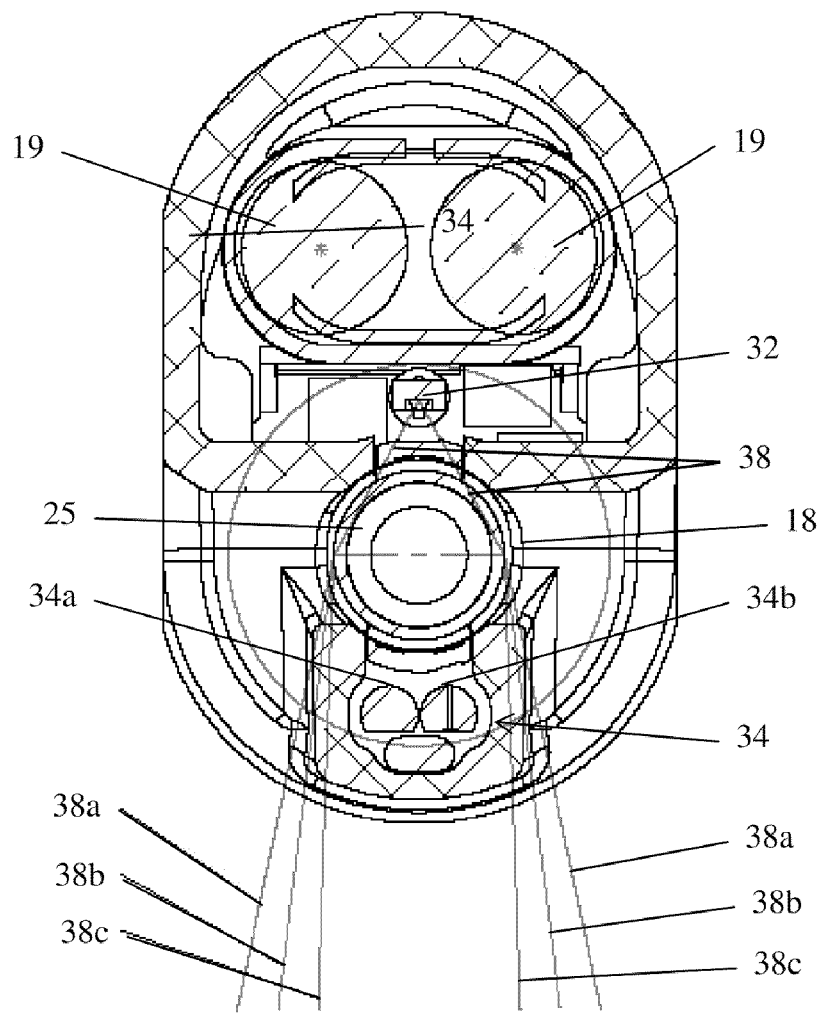
FIG. 3 illustrates optical testing by the tester assembly shown in FIG. 2, in accordance with embodiments of the present invention.

FIG. 3 illustrates optical testing by the tester assembly shown in FIG. 2, in accordance with embodiments of the present invention. Ampoule extension 25 may be positioned in ampoule cradle 18. When ampoule extension 25 is placed in ampoule cradle 18, radiation source 32 and detector assembly 34 are located on opposite sides of ampoule extension 25. Radiation source 32 may emit a conical diverging beam of radiation. For example, radiation source 32 may include a collimator or lens that shapes the emitted beam into a conical shape. The diverging beam in an optical plane that includes radiation source 32 and a detector of detector assembly 34 may be described as delimited by edge rays 38. Typically, radiation source 32 emits a pulsed beam of near infrared radiation. The radiation impinges on a surface of ampoule extension 25. At least part of the impinging radiation may traverse ampoule extension 25 to emerge from an opposite side of ampoule extension 25. At least part of the radiation emerging from ampoule extension 25 emerges toward detector assembly 34. When the beam traverses the circular cross section of ampoule extension 25, the edge rays 38 of the beam are bent toward each other. Thus the emerging beam tends to converge. The converging beam may be described as delimited by bent edge rays whose paths may depend on the fluid contents of ampoule extension 25. For example, when ampoule extension 25 is filled with a material with a low index of refraction, for example air, the bent edge rays may travel along the path indicated by bent edge rays 38a. When ampoule extension 25 is filled with a material with an intermediate index of refraction, for example water, the bent edge rays may travel along the path indicated by bent edge rays 38b. Finally, when ampoule extension 25 is filled with a material with high index of refraction, for example fuel of a particular grade, the bent edge rays may travel along the path indicated by bent edge rays 38c. Generally, the narrower the angle between the bent edge rays that delineate a beam, the greater the intensity the beam, and the greater the intensity of radiation impinging on detector assembly 34. Thus, in the example shown, when the fluid contents of ampoule extension 25 include primarily fuel, the intensity is greater than when the fluid contents are primarily water. Similarly, when the fluid contents are primarily water, the intensity is greater than when the fluid contents are primarily air. Thus, a signal generated by detector 34a or detector 34b may be interpreted to indicate whether the contents of ampoule extension 25 are primarily fuel, water, or air.

Figure 4:
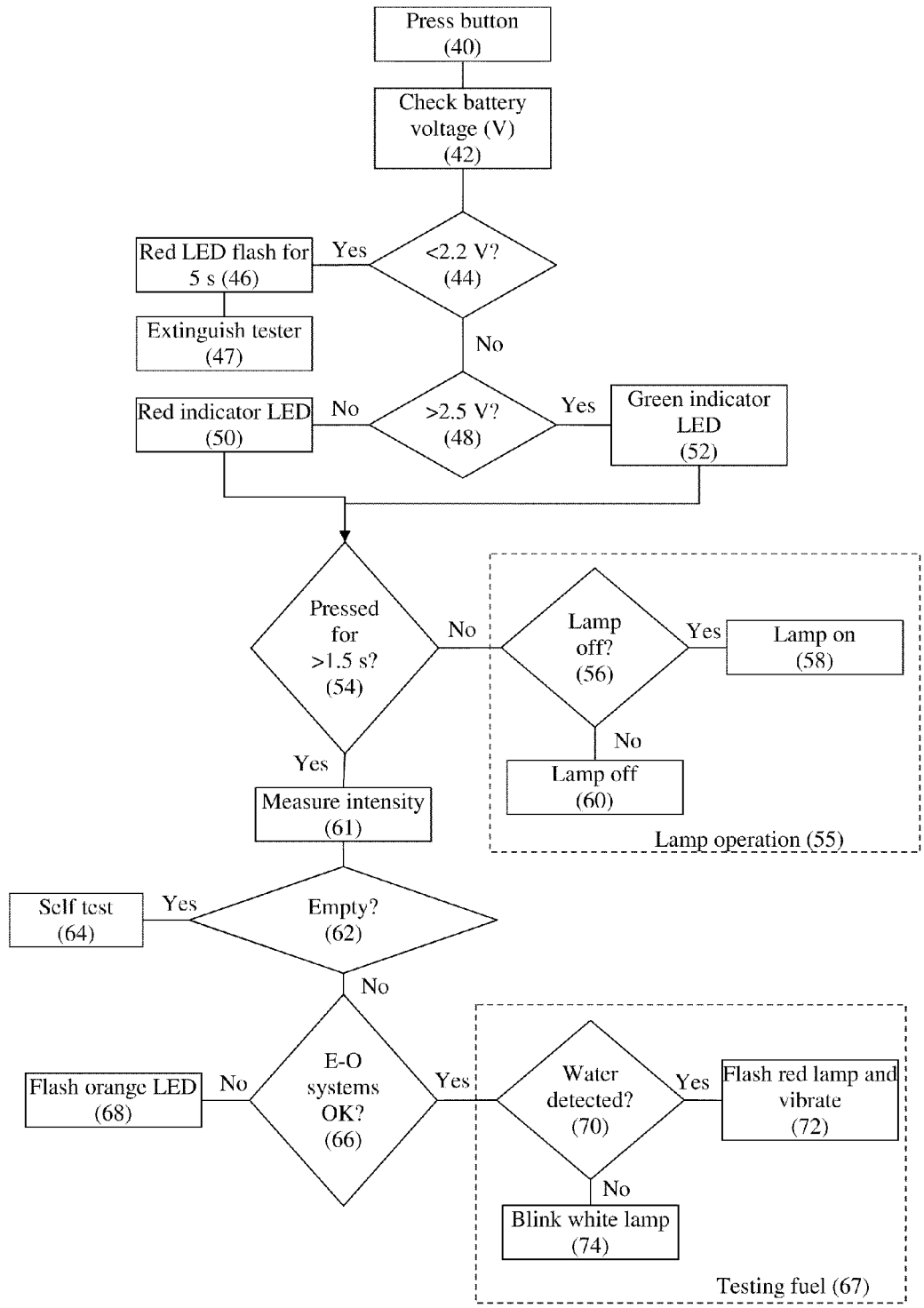
FIG. 4 is a flow chart of operation of a fluid tester in accordance with some embodiments of the present invention.

Typically, various components of a fluid tester are operated via a controller in accordance with a method of operation. Typically, the controller includes a programmed processor. The controller typically includes circuitry, as known in the art, for operating various components. FIG. 4 is a flow chart of a method of operation of a fluid tester in accordance with some embodiments of the present invention. It should be understood by one skilled in the art that the order of steps of the method of operation as illustrated in the flow chart is selected for illustration purposes only. Various steps of the method may be omitted or added, or various steps may be performed concurrently or in a different order, with the method yielding equivalent results.

In a typical configuration of a fluid tester, the fluid tester is operated by pressing a button (step 40), such as pushbutton 14 (FIG. 1A). Alternatively, a fluid tester may be provided with several controls, each operating one or more separate functions.

Upon activation of the fluid tester by pressing pushbutton 14, the controller measures the voltage of the battery by using a voltage measurement method such as is known in the art (step 42). The measured battery voltage may be below a predetermined minimum voltage, typically 2.2 V, considered a minimum voltage for proper operation of the fluid tester (step 44). The fluid tester may then issue an alert, for example by flashing a red LED of an indicator LED assembly for a predetermined period of time, typically 5 seconds (step 46). After issuing the alert, the fluid tester may then turn itself off (step 47).

The measured battery voltage may be greater than a minimum voltage, typically 2.5 V, indicating that the battery is fully charged (step 48). In this case, a suitable indication may be activated, typically by turning on a green indicator LED (step 52), and operation of the fluid tester continues. In the event that the measured battery voltage is sufficient for proper operation but the battery is not fully charged, typically between 2.2 V and 2.5 V, a suitable indication may be activated, typically by turning on a red indicator LED (step 50). In this case also, operation of the fluid tester continues.

In a typical configuration, the function of the controller may be determined by the length of time that pushbutton 14 is pressed (step 54). For example, a short press, typically less than 1.5 seconds, may cause the controller to operate an illumination lamp (step 55), such as white lamp 36 (FIG. 2) of illuminator 35 (FIG. 1C). For example, the lamp may be turned on in order to illuminate the contents of an ampoule for visual inspection. When pushbutton 14 is operated by a short press, the controller first determines whether the lamp is currently on or off (step 56). If the lamp is currently off, the controller turns the lamp on (step 58). On the other hand, if the lamp is currently on, the controller turns the lamp off (step 60).

In a typical configuration, in the event that pushbutton 14 is pressed for a long period of time, typically for longer than 1.5 seconds, the fluid tester may operate an automatic testing device. During operation of the automatic testing device, mode, a radiation source may be operated so as to irradiate a section of an ampoule. Concurrently, a detector assembly located on a side of the section of ampoule opposite the source generates a signal indicating the intensity of radiation that impinges on the detector assembly (step 61). Typically, the radiation source irradiates the section of the ampoule with pulsed radiation. In general, the radiation impinging on the detector assembly includes radiation from the source that had traversed the irradiated section of ampoule, as well as other stray or ambient radiation. An appropriate circuit or processor may be operated to extract from the total detector signal a signal that is correlated only to the intensity of the pulsed traversing radiation. The value of the measured intensity of the traversing radiation may be compared with a predetermined set of values. In general, the set of values may associate a measured intensity value with a possible composition of the ampoule contents, or with another state of the ampoule. For example, the measured intensity value may be less than a threshold value. A measured intensity value less than the threshold value may indicate that the ampoule is empty, or is filled with air (step 62).

If an empty ampoule is indicated, the fluid tester may perform a self test (step 64). For example, a self test procedure, as known in the art, may check the performance of various electronic components of the fluid tester. For example, a self test may include testing an electro-optic system of the fluid tester. For example, the measured intensity may be compared with the intensity expected for an ampoule filled with air. An unexpectedly low intensity may then indicate that one or more optical components are dirty, not operational, or misaligned. In the event that the fluid tester fails the self test, the test result indicating the failure may be stored in a memory component of the controller. Alternatively or in addition, the fluid tester may activate a suitable indication, for example, flashing an orange indicator LED.

The measured intensity value may indicate the presence of a liquid in the ampoule. For example, the measured intensity may greater than the expected intensity for air. The controller may then proceed to test the contents of the ampoule. The controller may first determine whether the electro-optic components and systems are operating properly (step 66). For example, the most recently saved self test results may be recalled. As another example, the system may check for a detector signal that indicates that the detector is saturated. If improper operation is found, the fluid tester may indicate that it is not possible to reliable test the ampoule contents. In a typical configuration, failure of the electro-optic system may be indicated by flashing an orange indicator LED (step 68).

If the electro-optical components are found to be working properly, the fluid tester proceeds to check the contents of the ampoule (step 67). The measured intensity may be compared with a predetermined intensity value that may indicate the presence of water in the ampoule (step 70). In the event that the fluid tester detector assembly includes several intensity detectors, the intensity measured by each detector may be separately compared with the expected intensity for water. If the intensity measured by one or more of the detectors indicates the presence of water in the ampoule, the fluid tester may operate one or more alarm indicators for a predetermined period of time. Operation of an alarm indicator may indicate the unacceptable presence of water in the fuel system, or a different unacceptable composition of the fluid sample (step 72). Typically, the alarm indicator may include illuminating the ampoule with a flashing red lamp, such as red lamp 37 (FIG. 2). In addition, the fluid tester may vibrate, providing an indication that is both audible and palpably sensible. In the event that the detected intensity indicates that the ampoule contains fuel of a particular type, the fluid tester may indicate that the ampoule contains fuel with an acceptable composition (step 74). Typically, the indication may include illuminating the ampoule with a slowly blinking white lamp, such as white lamp 36, for a predetermined period of time.

After an indicator or other component of the fluid tester has operated for a predetermined period of time, the fluid tester may extinguish all components. Alternatively, the fluid tester may switch operation to a standby mode. For example, operation of all components may be stopped, except for an indicator LED.

It should be clear that the description of the embodiments and attached Figures set forth in this specification serves only for a better understanding of the invention, without limiting its scope.

It should also be clear that a person skilled in the art, after reading the present specification could make adjustments or amendments to the attached Figures and above described embodiments that would still be covered by the present invention.

The invention claimed is:

1. An optical fluid tester device for testing a fluid sample in an ampoule, the device comprising:
    an ampoule cradle for supporting the ampoule, the ampoule with the fluid sample serving as a lens whose focal properties are dependent on the index of refraction of the fluid sample;
    a radiation source for irradiating the ampoule;
    two or more radiation detectors located opposite the radiation source and positioned in known positions with respect to each other, so that the ampoule, when supported by the ampoule cradle, lies between the radiation source and the radiation detectors, the detectors serving for detecting intensities of incident radiation; and
    an analyzer for verifying the composition of the fluid sample based on the detected intensities which is dependent on the focal properties of the ampoule and the known positions of the detectors, thereby indicative of the composition of the fluid sample.

2. A device as claimed in claim 1 comprising an illuminator lamp for illuminating the fluid sample in the ampoule.

3. A device as claimed in claim 2, wherein the illuminator lamp is configured so as to illuminate the fluid sample from below the ampoule and an area above the ampoule.

4. A device as claimed in claim 1, wherein the ampoule cradle allows visual inspection of the ampoule and the fluid inside.

5. A device as claimed in claim 1, wherein the radiation source is configured to emit radiation with a spectral range of 800 nm to 1000 nm.

6. A device as claimed in claim 1, wherein the analyzer is configured to distinguish between water and a fuel.

7. A device as claimed in claim 1, comprising an indicator for indicating the composition of the fluid sample.

8. A device as claimed in claim 7, wherein the indicator comprises a blinking white lamp for indicating an acceptable composition.

9. A device as claimed in claim 7, wherein the alarm comprises a flashing red lamp for indicating an unacceptable composition.

10. A device as claimed in claim 1, comprising a circuitry for verifying an operational condition of the device.

11. A device as claimed in claim 10, comprising a light emitting diode assembly for indicating the operation condition.

12. A device as claimed in claim 1, wherein the radiation source is configured to emit radiation with a predetermined pulse pattern and wherein the analyzer is configured to verify the composition of the fluid sample based on detected intensity with a pulse pattern substantially matching the predetermined pulse pattern.

13. A device as claimed in claim 1, wherein the radiation source is configured to emit a diverging beam of radiation.

14. A device as claimed in claim 1, wherein the device is configured to be operated by pressing on a single pushbutton.

15. A device as claimed in claim 14, wherein the device is configured to distinguish between a short press and a long press on the pushbutton, such that operation of the device is controllable by the length of the press.

16. A device as claimed in claim 1, wherein the device is configured to run a self test when the verified composition is consistent with the composition of the contents of an empty ampoule.

17. A device as claimed in claim 1, wherein said two or more detectors are arranged such that at least one of said two or more detectors is located at a higher position with respect to the position of at least one other detector of said two or more detectors.

* * * * *